US012588812B2

(12) United States Patent
Takahashi et al.

(10) Patent No.: US 12,588,812 B2
(45) Date of Patent: Mar. 31, 2026

(54) OPHTHALMIC APPARATUS, METHOD OF CONTROLLING SAME, AND RECORDING MEDIUM

(71) Applicant: Topcon Corporation, Tokyo (JP)

(72) Inventors: Akira Takahashi, Tokyo (JP); Kazuhiro Yamada, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 641 days.

(21) Appl. No.: 17/872,038

(22) Filed: Jul. 25, 2022

(65) Prior Publication Data

US 2022/0354365 A1     Nov. 10, 2022

Related U.S. Application Data

(63) Continuation of application No. PCT/JP2021/008667, filed on Mar. 5, 2021.

(30) Foreign Application Priority Data

Mar. 13, 2020   (JP) ................................. 2020-043604

(51) Int. Cl.
| | |
|---|---|
| A61B 3/12 | (2006.01) |
| A61B 3/00 | (2006.01) |
| A61B 3/14 | (2006.01) |

(52) U.S. Cl.
CPC .............. *A61B 3/12* (2013.01); *A61B 3/0025* (2013.01); *A61B 3/14* (2013.01); *A61B 2560/0214* (2013.01)

(58) Field of Classification Search
CPC ........... A61B 3/12; A61B 3/0025; A61B 3/14; A61B 2560/0214; A61B 3/10; A61B 3/1025
See application file for complete search history.

(56) References Cited

U.S. PATENT DOCUMENTS

| | | | |
|---|---|---|---|
| 4,021,102 A | 5/1977 | Iizuka | |
| 4,732,466 A | 3/1988 | Humphrey | |

(Continued)

FOREIGN PATENT DOCUMENTS

| | | |
|---|---|---|
| CN | 108652581 A | 10/2018 |
| CN | 109924942 A | 6/2019 |

(Continued)

OTHER PUBLICATIONS

Extended European Search Report issued Feb. 27, 2024, in corresponding European Patent Application 21766851.6, 12pp.

(Continued)

*Primary Examiner* — Bumsuk Won
*Assistant Examiner* — John Curtis Sipes
(74) *Attorney, Agent, or Firm* — XSENSUS LLP

(57)     ABSTRACT

An ophthalmic apparatus includes a light source, an illumination optical system, an optical scanner, an imaging optical system, and a controller. The illumination optical system is configured to generate slit-shaped illumination light using light from the light source. The optical scanner is configured to deflect the illumination light to guide the illumination light to a fundus of a subject's eye. The imaging optical system is configured to guide returning light of the illumination light from the fundus to an image sensor, the image sensor capturing light receiving result of a region on a light receiving surface corresponding to an illumination region of the illumination light on the fundus, the illumination region being moved by the optical scanner. The controller is configured to control a deflection angle of the illumination light of the optical scanner. The optical scanner is configured to output a scanner position signal corresponding to the deflection angle of the illumination light. The image sensor is configured to start capturing the light receiving result of (Continued)

the returning light in synchronization with the scanner position signal.

15 Claims, 12 Drawing Sheets

(56)                    References Cited

U.S. PATENT DOCUMENTS

| | | | |
|---|---|---|---|
| 7,831,106 | B2 | 11/2010 | Elsner et al. |
| 8,237,835 | B1 | 8/2012 | Muller |
| 2003/0231285 | A1 | 12/2003 | Ferguson |
| 2004/0036838 | A1 | 2/2004 | Podoleanu et al. |
| 2009/0009715 | A1 | 1/2009 | Mensink |
| 2009/0244482 | A1 | 10/2009 | Elsner et al. |
| 2010/0110171 | A1 | 5/2010 | Satake |
| 2010/0128221 | A1 | 5/2010 | Muller et al. |
| 2013/0222763 | A1 | 8/2013 | Bublitz et al. |
| 2014/0232987 | A1 | 8/2014 | Westphal et al. |
| 2015/0085252 | A1 | 3/2015 | Fujimura et al. |
| 2016/0345822 | A1 | 12/2016 | Fujimura et al. |
| 2020/0214558 | A1 | 7/2020 | Wang et al. |
| 2022/0007935 | A1* | 1/2022 | Minamide ............ A61B 5/4893 |
| 2022/0175245 | A1* | 6/2022 | Soma ........................ A61B 3/08 |
| 2022/0217277 | A1 | 7/2022 | Zhang |

FOREIGN PATENT DOCUMENTS

| | | | |
|---|---|---|---|
| JP | S5084092 | A | 7/1975 |
| JP | S5529316 | A | 3/1980 |
| JP | 61-276534 | A | 12/1986 |
| JP | 61-293430 | A | 12/1986 |
| JP | 2000-135200 | A | 5/2000 |
| JP | 2005-531346 | A | 10/2005 |
| JP | 2009-538697 | A | 11/2009 |
| JP | 2010-259495 | A | 11/2010 |
| JP | 2012-187293 | A | 10/2012 |
| JP | 2013-248376 | A | 12/2013 |
| JP | 2014-68704 | A | 4/2014 |
| JP | 2017-196302 | A | 11/2017 |
| WO | 2018/113585 | A1 | 6/2018 |

OTHER PUBLICATIONS

Japanese Office Action issued Mar. 26, 2024, in corresponding Japanese Patent Application 2020-043604, 7pp.
International Search Report and Written Opinion mailed on May 25, 2021, received for PCT Application PCT/JP2021/008667, filed on Mar. 5, 2021, 11 pages including English Translation.
Japanese Office Action issued Aug. 27, 2024, in corresponding Japanese Patent Application No. 2020-043604, 5pp.
Chinese Office Action issued Jan. 25, 2025, in corresponding Chinese Patent Application No. 202180020977.8, 13pp.

* cited by examiner

OPHTHALMIC APPARATUS, METHOD OF CONTROLLING SAME, AND RECORDING MEDIUM

CROSS-REFERENCE TO RELATED APPLICATIONS

The present application is a continuation application of International Patent Application No. PCT/JP2021/008667, filed Mar. 5, 2021, which claims priority to Japanese Patent Application No. 2020-043604, filed Mar. 13, 2020, both of which are herein incorporated by reference in their entirety.

FIELD

The disclosure relates to an ophthalmic apparatus, a method of controlling the same, and a program.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired.

For example, U.S. Pat. Nos. 7,831,106 and 8,237,835 disclose an ophthalmic apparatus configured to pattern-illuminate a subject's eye using slit light and to detect returning light of the slit light using a CMOS (Complementary Metal Oxide Semiconductor) image sensor. This ophthalmic apparatus can acquire images of the subject's eye with a simple configuration, by adjusting the illumination pattern and the timing of light receiving timing using the CMOS image sensor.

SUMMARY

One aspect of some embodiments is an ophthalmic apparatus, including: a light source; an illumination optical system configured to generate slit-shaped illumination light using light from the light source; an optical scanner configured to deflect the illumination light to guide the illumination light to a fundus of a subject's eye; an imaging optical system configured to guide returning light of the illumination light from the fundus to an image sensor, the image sensor capturing light receiving result of a region on a light receiving surface corresponding to an illumination region of the illumination light on the fundus, the illumination region being moved by the optical scanner; and a controller configured to control a deflection angle of the illumination light of the optical scanner, wherein the optical scanner is configured to output a scanner position signal corresponding to the deflection angle of the illumination light, and the image sensor is configured to start capturing the light receiving result of the returning light in synchronization with the scanner position signal.

Another aspect of some embodiments is a method of controlling an ophthalmic apparatus including: a light source; an illumination optical system configured to generate slit-shaped illumination light using light from the light source; an optical scanner configured to deflect the illumination light to guide the illumination light to a fundus of a subject's eye; an imaging optical system configured to guide returning light of the illumination light from the fundus to an image sensor, the image sensor capturing light receiving result of a region on a light receiving surface corresponding to an illumination region of the illumination light on the fundus, the illumination region being moved by the optical scanner; and a controller configured to control a deflection angle of the illumination light of the optical scanner, the method comprising: a first output step of outputting a scanner position signal corresponding to a deflection angle of the illumination light by the optical scanner, and a light receiving result acquisition step of starting capturing light receiving result of the returning light in synchronization with the scanner position signal by the image sensor by the image sensor. The method of controlling the ophthalmic apparatus includes a first output step of outputting a scanner position signal corresponding to a deflection angle of the illumination light by the optical scanner, and a light receiving result acquisition step of starting capturing light receiving result of the returning light in synchronization with the scanner position signal by the image sensor.

Still another aspect of some embodiments is a program of causing a computer to execute each step of the method of controlling the ophthalmic apparatus described above.

DETAILED DESCRIPTION

Figure 1:
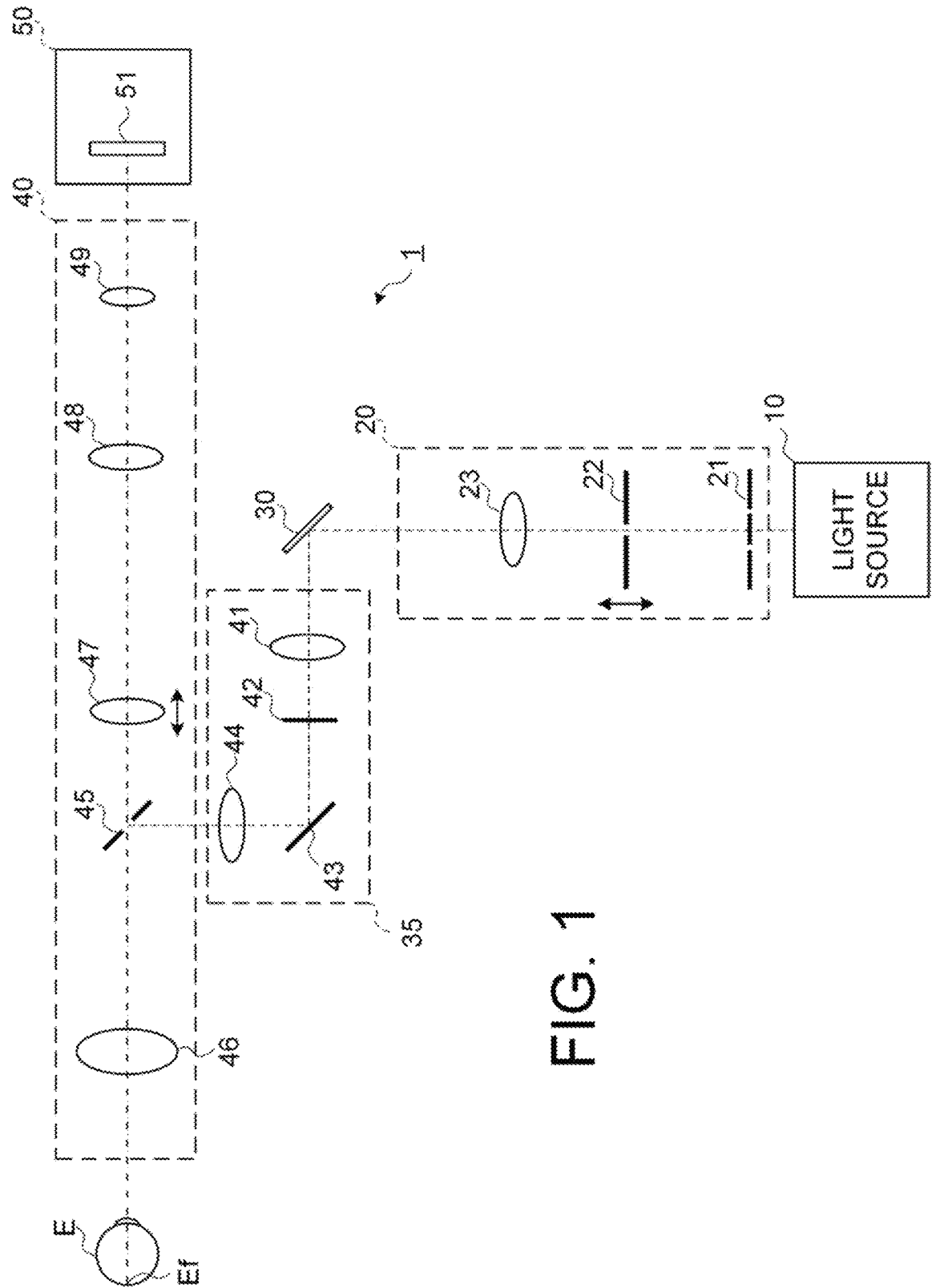
FIG. 1 is a schematic diagram illustrating an example of a configuration of an optical system of an ophthalmic apparatus according to a first embodiment.

In this type of ophthalmic apparatuses, returning light of illumination light is received and is captured at the appropriate timing in the CMOS image sensor. Thereby, the effect of unnecessary scattered light can be eliminated and the image quality of the acquired image of the subject's eye can be improved.

However, in the conventional method, the control for the illuminating side and the control for the light receiving side cannot be synchronize with high precision. Thereby, it is necessary to receive and to capture the returning light in consideration of the time gap between the control for the illuminating side and the control for the light receiving side. And unnecessary scattered light is received. As a result, the image quality of the acquired images of the subject's eye is degraded.

According to some embodiments according to the present invention, a new technique for acquiring a high quality image of a subject's eye with a simple configuration can be provided.

Referring now to the drawings, exemplary embodiments of an ophthalmic apparatus, a method of controlling the same, and a program according to the present invention are described below. The contents of the document cited in the present specification can be appropriately incorporated as contents of the following embodiments.

An ophthalmic apparatus according to embodiments illuminates a predetermined site of a subject's eye while moving an irradiated position (illumination region, irradiated range) of slit-shaped illumination light, and receives returning light from the predetermined site using an image sensor with a one-dimensional or two-dimensional array of light receiving elements. Light receiving result of the returning light is read out from the light receiving elements at light receiving position of the returning light corresponding to the irradiated position of the illumination light, in synchronization with the movement timing of the irradiated position of the illumination light. In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, a case where the ophthalmic apparatus according to the embodiments acquires images of the fundus of the subject's eye mainly will be described. In the ophthalmic apparatus according to a first embodiment, an optical scanner and a light receiving element (image element) are synchronized with high precision to improve the image quality of the acquired images. In the ophthalmic apparatus according to a second embodiment, the optical scanner, the light receiving element, and a light source are synchronized with high precision to improve the image quality of the acquired images.

First Embodiment

[Configuration of Optical System]

Figure 2:
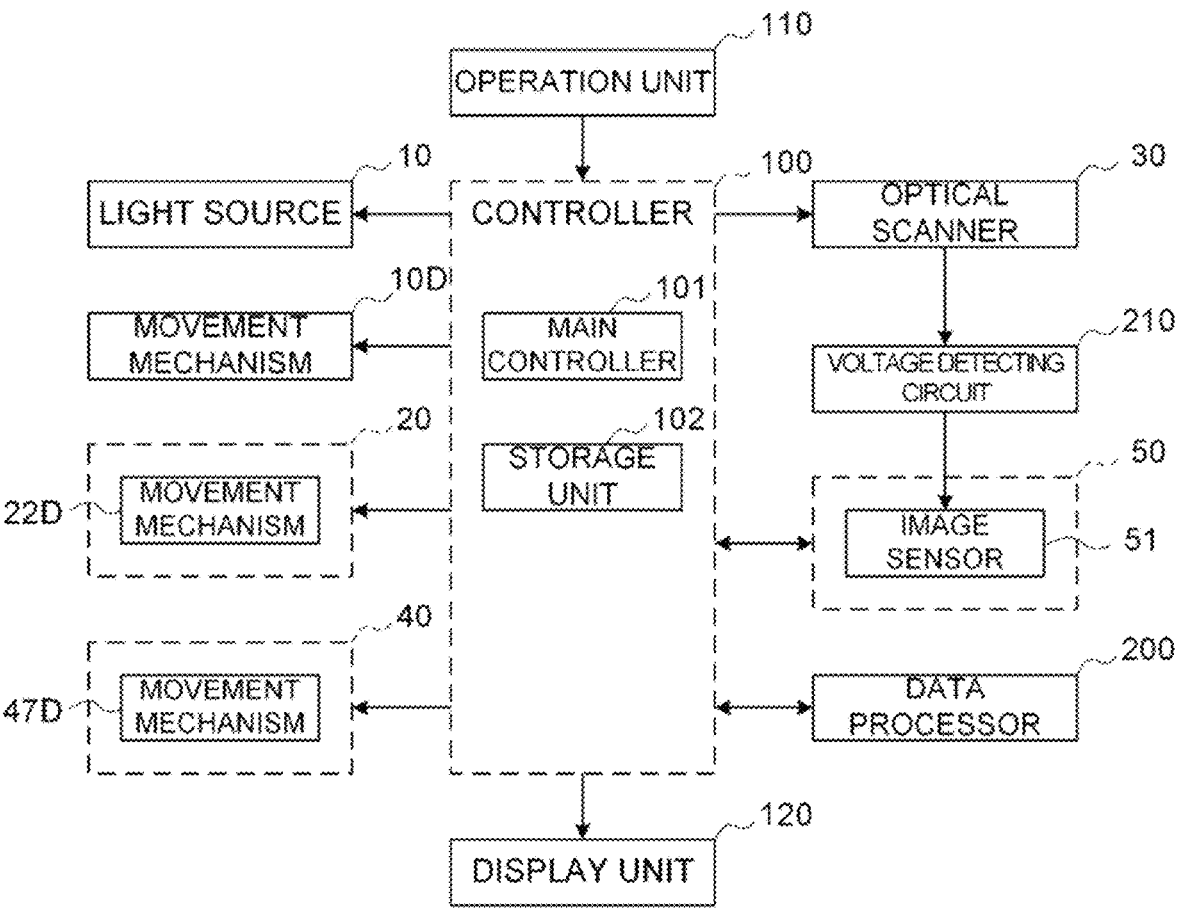
FIG. 2 is a schematic diagram illustrating an example of a configuration of a control system of the ophthalmic apparatus according to the first embodiment.
Figure 3:
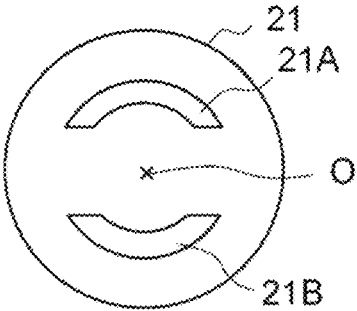
FIG. 3 is a schematic diagram illustrating an example of a configuration of an optical system of the ophthalmic apparatus according to the first embodiment.

FIGS. 1 to 3 show schematic diagrams of an example of a configuration of the ophthalmic apparatus according to the first embodiment. FIG. 1 represents an example of the configuration of an optical system of the ophthalmic apparatus 1 according to the first embodiment. FIG. 2 representing a block diagram of an example of the configuration of the control system (processing system) of the ophthalmic apparatus 1 according to the first embodiment. FIG. 3 schematically represents an example of the configuration of an iris aperture 21 in FIG. 1 when viewed from a direction of an optical axis O. In FIGS. 1 to 3, like parts are designated by like reference numerals as in repetitious description of such parts may not be provided.

The ophthalmic apparatus 1 includes a light source 10, an illumination optical system 20, an optical scanner 30, a projection optical system 35, and an imaging optical system 40, and an imaging device 50. In some embodiments, the illumination optical system 20 includes at least one of the light source 10, the optical scanner 30, or the projection optical system 35. In some embodiments, the imaging optical system 40 includes the imaging device 50. In some embodiments, the projection optical system 35 or the imaging optical system 40 includes the optical scanner 30.

(Light Source 10)

The light source 10 includes a visible light source that generates light in the visible region. For example, the light source 10 generates light having a central wavelength in the wavelength range of 420 nm to 700 nm. This type of light source 10 includes, for example, an LED (Light Emitting Diode), an LD (Laser Diode), a halogen lamp, or a xenon lamp. In some embodiments, the light source 10 includes a white light source or a light source capable of outputting light with each color component of RGB. In some embodiments, the light source 10 includes a light source capable of switching to output the light in infrared region or the light in visible region. The light source 10 is arranged at a position non-conjugate optically to each of a fundus Ef and the iris.

(Illumination Optical System 20)

The illumination optical system 20 generates slit-shaped illumination light using the light from the light source 10. The illumination optical system 20 guides the generated illumination light to the optical scanner 30.

The illumination optical system 20 includes the iris aperture 21, the slit 22, and a relay lens 23. The light from the light source 10 passes through the aperture(s) formed in the iris aperture 21, passes through the aperture formed in the slit 22, and is transmitted through the relay lens 23. The relay lens 23 includes one or more lenses. The light transmitted through the relay lens 23 is guided to the optical scanner 30.

(Iris Aperture 21)

The iris aperture 21 (specifically, aperture(s) described below) can be arranged at a position substantially conjugate optically to the iris (pupil) of a subject's eye E. In the iris aperture 21, one or more apertures are formed at position(s) away from the optical axis O. For example, as shown in FIG. 3, apertures 21A and 21B having a predetermined thickness along a circumferential direction centered with the optical axis O are formed in the iris aperture 21. The aperture(s) formed in the iris aperture 21 defines an incident position (incident shape) of the illumination light on the iris of the subject's eye E. For example, when the pupil center of the subject's eye E is arranged on the optical axis O, the illumination light can enter into the eye from positions deviated from the pupil center (specifically, point-symmetrical positions centered on the pupil center), by forming the apertures 21A and 21B as shown in FIG. 3.

Further, the light amount distribution of the light passing through the aperture(s) formed in the iris aperture 21 can be changed by changing a relative position between the light source 10 and the aperture(s) formed in the iris aperture 21.

(Slit 22)

The slit 22 (specifically, aperture(s) described below) can be arranged at a position substantially conjugate optically to the fundus Ef of the subject's eye E. For example, in the slit 22, the aperture is formed extending in a direction corresponding to a line direction (row direction) that is read out from the image sensor 51 described below using the rolling shutter method. The aperture formed in the slit 22 defines an irradiated pattern of the illumination light on the fundus Ef of the subject's eye E.

The slit 22 can be moved in the optical axis direction of the illumination optical system 20 using a movement mechanism (movement mechanism 22D described below). The movement mechanism moves the slit 22 in the optical axis direction, under the control from the controller 100 described below. For example, the controller 100 controls the movement mechanism in accordance with the state of the subject's eye E. This allows to move the position of the slit 22 in accordance with the state of the subject's eye E (specifically, the dioptric power or the shape of the fundus Ef).

In some embodiments, the slit 22 is configured so that at least one of the position of the aperture or the shape of the aperture can be changed in accordance with the state of the subject's eye E without being moved in the optical axis direction. The function of the slit 22 with this configuration is, for example, realized by a liquid crystal shutter.

The light from the light source 10 that has passed through the aperture(s) formed in the iris aperture 21 is output as the slit-shaped illumination light by passing through the aperture formed in the slit 22. The slit-shaped illumination light is transmitted through the relay lens 23, and is guided to the optical scanner 30.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture formed in the slit 22). Specifically, the optical scanner 30 deflects the slit-shaped illumination light for sequentially illuminating a predetermined illumination region of the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illumination light one-dimensionally or two-dimensionally.

In case that the optical scanner 30 deflects the illumination light one-dimensionally, the optical scanner 30 includes a galvano scanner that deflects the illumination light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the illumination optical system 20. The second galvano scanner deflects light deflected by the first galvano scanner so as to move the irradiated position of the illumination light in a vertical direction orthogonal to the optical axis of the illumination optical system 20. Examples of scan mode for moving the irradiated position of the illumination light using the optical scanner 30 include a horizontal scan, a vertical scan, a cross scan, a radial scan, a circle scan, a concentric scan, and a helical (spiral) scan.

The optical scanner 30 is a non-resonant optical scanner, for example. In this case, the controller 100 described below can set one or more orientations of a deflection surface of the optical scanner 30 so as to irradiate the illumination light onto a desired irradiated range. The optical scanner 30 can change a deflection angle (deflection angle of the deflection surface) of the illumination light by changing the orientation of the deflection surface under the control from the controller 100 described below, and can output a scanner position signal Spos having a voltage level corresponding to the deflection angle.

In some embodiments, the optical scanner 30 is a resonant optical scanner, for example. In this case, the controller 100 described below can set the orientation of the deflection surface of a scan center, and a scan range with reference to the scan center to the optical scanner 30, so as to irradiate the illumination light onto the desired irradiated range. The optical scanner 30 can change a deflection angle (deflection angle of the deflection surface) of the illumination light by changing the orientation of the deflection surface under the control from the controller 100 described below, and can output a scanner position signal Spos having a voltage level corresponding to the deflection angle.

(Projection Optical System 35)

The projection optical system 35 guides the illumination light deflected by the optical scanner 30 to the fundus Ef of the subject's eye E. In the embodiments, the projection optical system 35 guides the illumination light deflected by the optical scanner 30 through an optical path coupled with an optical path of the imaging optical system 40 by a perforated mirror 45 as the optical path coupling member described below.

The projection optical system 35 includes a relay lens 41, a black point plate 42, a reflective mirror 43, and a relay lens 44. Each of the relay lenses 41 and 44 includes one or more lenses.

(Black Point Plate 42)

The black point plate 42 is arranged at a position substantially conjugate optically to a lens surface of an objective lens 46 or the vicinity of the lens surface of the objective lens 46. This prevents the reflected light from the lens surface of the objective lens 46 from being guided to the light source 10 (illumination optical system 20).

With such projection optical system 35, the illumination light deflected by the optical scanner 30 is transmitted through the relay lens 41, passes through the black point plate 42, is reflected by the reflective mirror 43 toward the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, a focusing lens 47, a relay lens 48, and an imaging lens 49. Each of relay lens 48 includes one or more lenses.

(Perforated Mirror 45)

In the perforated mirror 45, the hole is formed. The hole is arranged on the optical axis of the imaging optical system 40. The hole of the perforated mirror 45 is arranged at a position substantially conjugate optically to the iris of the subject's eye E. The perforated mirror 45 reflects the illumination light from the projection optical system 35 toward the objective lens 46, on the peripheral region of the hole.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light from the projection optical system 35 is reflected toward the objective lens 46 on the peripheral region of the hole formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, and is imaged on the light receiving surface of the image sensor 51 in the imaging device 50 through the imaging lens 49.

(Imaging Device 50)

The imaging device 50 includes the image sensor 51 receiving the returning light of the illumination light that has been guided from the fundus Ef of the subject's eye E through the imaging optical system 40. The imaging device 50 can output the light receiving result of the returning light under the control from the controller 100 described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result acquired by the image sensor 51 is read out using a rolling shutter method. In some embodiments, the controller 100 described below performs readout control of the light receiving result by controlling the image sensor 51. In some embodiments, the image sensor 51 can automatically output the light receiving results for a predetermined number of lines, along with information indicating the light receiving position(s).

The image sensor 51 with this configuration includes the CMOS image sensor. In this case, the image sensor 51 includes a plurality of pixels (light receiving elements). The plurality of pixels includes a plurality of pixel groups arranged in a column direction. Each of the plurality of pixel groups includes pixels arranged in a row direction. Specifically, the image sensor 51 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual opening shape extending in the row direction is acquired. Such control is disclosed in, for example, U.S. Pat. No. 8,237,835.

Figure 4:
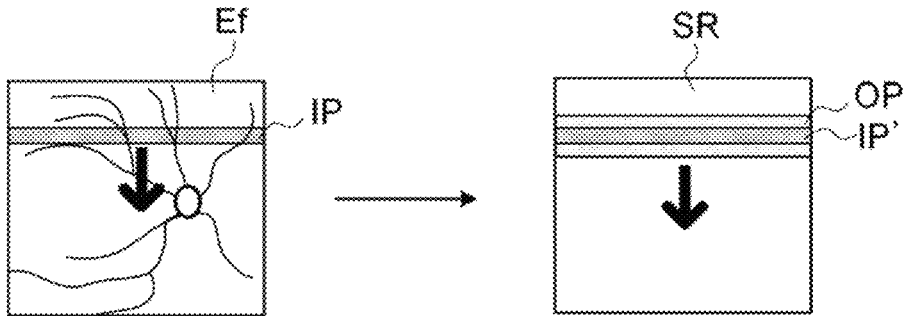
FIG. 4 is an explanatory diagram of an operation of the ophthalmic apparatus according to the first embodiment.

FIG. 4 shows a diagram describing the operation of the ophthalmic apparatus 1 according to the first embodiment. FIG. 4 schematically represents an irradiated range IP of the slit-shaped illumination light irradiated on the fundus Ef and a virtual opening range OP on the light receiving surface SR of the image sensor 51.

For example, the controller 100 described below deflects the slit-shaped illumination light formed by the illumination optical system 20, using the optical scanner 30. Thereby, the irradiated range IP of the slit-shaped illumination light is sequentially moved in a direction (for example, the vertical direction) orthogonal to the slit direction (for example, the row direction, the horizontal direction) on the fundus Ef.

On the light receiving surface SR of the image sensor 51, for example, by changing the pixels to be captured in units of lines by the controller 100 described below, the virtual opening range OP is set. The opening range OP is preferable to be the light receiving range IP' of the returning light of the illumination light on the light receiving surface SR or wider than the light receiving range IP'. For example, the controller 100 described below performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

Figure 5:
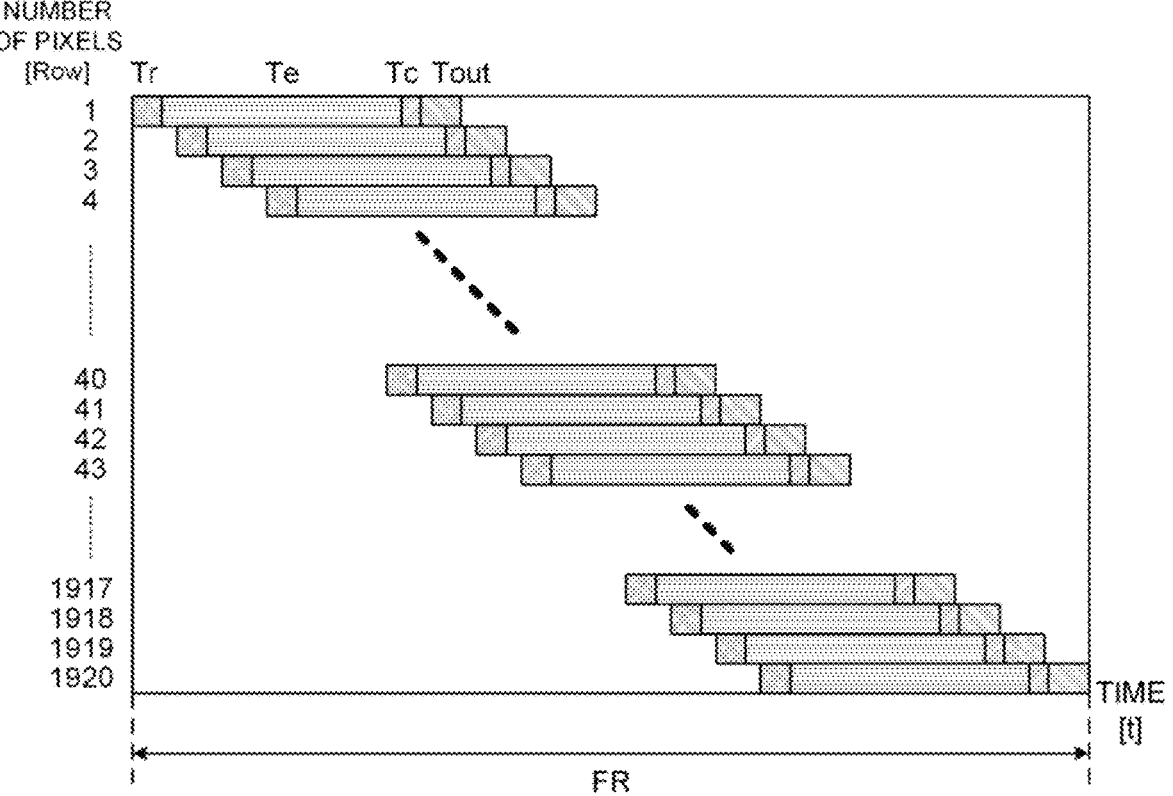
FIG. 5 is an explanatory diagram of an operation of the ophthalmic apparatus according to the first embodiment.
Figure 6:
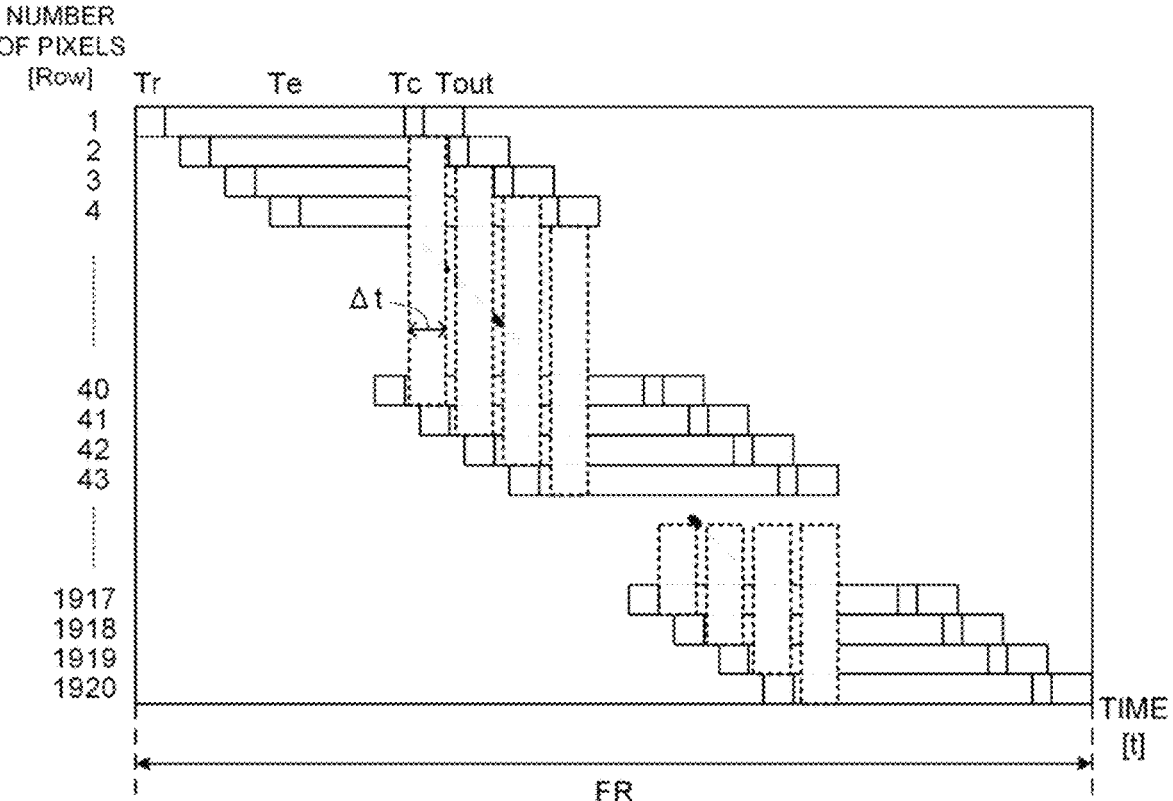
FIG. 6 is an explanatory diagram of an operation of the ophthalmic apparatus according to the first embodiment.

FIGS. 5 and 6 schematically show examples of the control timing of the rolling shutter method for the image sensor 51. FIG. 5 represents an example of the timing of the readout control for the image sensor 51. FIG. 6 represents the timing of the movement control for the irradiated range IP (the light receiving range IP') superimposed on the timing of the readout control in FIG. 5. In FIGS. 5 and 6, the horizontal axis represents the number of rows in the image sensor 51, and the vertical axis represents time.

In addition, in FIGS. 5 and 6, for convenience of explanation, it is assumed that the number of rows in the image sensor 51 is 1920. However, the configuration according to the first embodiment is not limited to the number of rows. Further, in FIG. 6, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 5, the readout time T for reading out the electrical charge accumulated in the pixels in the row direction is the sum of the time Tr required for the reset control, the time Te required for the exposure control (exposure time), the time Tc required for the charge transfer control, and the time Tout required for the output control.

In FIG. 5, by shifting the readout (capturing) start timing (start timing of time Tc) in units of rows, the light receiving results (amount of electrical charge) accumulated in the pixels in the desired range in the image sensor 51 are acquired. For example, in case that the pixel range shown in FIG. 5 is for a single frame of the image, the frame rate FR is determined uniquely.

In this embodiment, the irradiated position of the illumination light on the fundus Ef, the illumination light having a slit width of a plurality of rows, is sequentially shifted in a direction corresponding to the column direction on the fundus Ef.

For example, as shown in FIG. 6, at each predetermined shift time Δt, the irradiated position of the illumination light on the fundus Ef is shifted in row units in the direction corresponding to the column direction. The shift time Δt is obtained by dividing the exposure time Te of the pixel in the image sensor 51 by the slit width (e.g., the number of rows of the slit width=40) of the illumination light (Δt=Te/40). Synchronized with this movement timing of this irradiated position, the readout start timing of each row of pixels is delayed and is started for each row in units of shift time Δt. This allows to acquired high quality images of the fundus Ef with strong contrast in a short time with a simple control.

In some embodiments, the image sensor 51 is configured using one or more line sensors.

[Configuration of Control System]

As shown in FIG. 2, the control system of the ophthalmic apparatus 1 is configured with a controller 100 as a center. It should be noted that at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs a control for the light source 10, a control for a movement mechanism 10D, a control for the illumination optical system 20, a control for the optical scanner 30, a control for the imaging optical system 40, a control for the imaging device 50, a control for data processor 200, and a control for a voltage detecting circuit 210.

The control for the light source 10 includes switching the light source on and off (or switching the wavelength region of the light), and changing the light amount of the light source.

The movement mechanism 10D changes at least one of the position of the light source 10 or the orientation of the light source 10 using a known mechanism. The main controller 101 can change at least one of a relative position of the light source 10 to the iris aperture 21 and the slit 22, or a relative orientation of the light source 10 to the iris aperture 21 and the slit 22.

The control for the illumination optical system 20 includes control for a movement mechanism 22D. The movement mechanism 22D moves the slit 22 in the optical axis direction of the illumination optical system 20. The main controller 101 controls the movement mechanism 22D in accordance with the state of the subject's eye E to arrange the slit 22 at the position corresponding to the state of the subject's eye E. Examples of the state of the subject's eye E includes a shape of the fundus Ef, a dioptric power, and an axial length. The dioptric power can be obtained from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the dioptric powers in advance. The main controller 101 specifies the position of the slit 22 corresponding to the dioptric power by referring to the first control information, and controls the movement mechanism 22D so as to arrange the slit 22 at the specified position.

Here, as the slit 22 moves, the light amount distribution of the light passing through the aperture formed in the slit 22 changes. In this case, as described above, the main controller 101 can control the movement mechanism 10D to change at least one of the position of the light source 10 or the orientation of the light source 10.

The control for the optical scanner 30 includes control of the angle of the deflection surface deflecting the illumination light. By controlling an angle range of the deflection surface, the scan range (scan start position and scan end position) can be controlled. By controlling a change speed of the angle of the deflection surface, the scan speed can be controlled.

The control for the imaging optical system 40 includes a control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 51. Further, the main controller 101 can control the movement mechanism 47D based on a content of operation of the user using an operation unit 110 described below.

The control for the imaging device 50 includes a control for the image sensor 51. The control for the image sensor 51 includes a control for reading out the light receiving result using a rolling shutter method (for example, setting of light receiving size corresponding to the size of the illumination pattern, or the like). Further, the control for the image sensor 51 includes the reset control, the exposure control, the charge transfer control, and the output control. The time Tr required for the reset control, the time (exposure time) Te required for the exposure control, the time Tc required for the charge transfer control, and the time Tout required for the output control, etc., can be changed.

Examples of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results. Examples of the analysis processing include a specifying processing of the in-focus state.

The data processor 200 can form the light receiving image corresponding to the arbitrary opening range based on the light receiving result(s) read out from the image sensor 51 using the rolling shutter method. The data processor 200 can sequentially form light receiving light images corresponding to the opening ranges and can form an image of the subject's eye E from a plurality of formed light receiving images, as an image forming unit.

The data processor 200 includes a processor, and realizes the above functions by performing processing corresponding to the program(s) stored in the storage unit or the like.

The voltage detecting circuit 210 outputs a trigger signal to the image sensor 51, as described below. The trigger signal instructs the image sensor 51 to start capturing the light receiving result(s) based on the scanner position signal from the optical scanner 30. The deflection angle of the illumination light changed by the optical scanner 30 can be specified from the scanner position signal. The function of the voltage detecting circuit 210 can be realized by a known comparator circuit. The control for such the voltage detecting circuit 210 includes setting a threshold voltage for determining whether or not the deflection angle of the illumination light changed by the optical scanner 30 is a desired deflection angle based on the scanner position signal, and the like.

In some embodiments, the light source 10 includes two or more light sources. In this case, each of the two or more light sources is provided corresponding to the two or more apertures formed in the iris aperture 21. The main controller 101 can change the at least one of a position of each light source or an orientation (orientation in the direction of maximum light amount distribution) of each light source, by controlling the movement mechanisms provided for each of the two or more light sources.

(Storage Unit 102)

The storage unit 102 stores various computer programs and data. The computer programs include an arithmetic program and a control program for controlling the ophthalmic apparatus 1.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content for the operation unit 110 is fed to the controller 100 as electrical signals. Moreover, operations and inputs of information may be performed using a graphical user interface (GUI) displayed on the display unit 120 and the operation unit 110. In some embodiments, the functions of the display unit 120 and the operation unit 110 are realized a touch screen.

(Other Configurations)

In some embodiments, the ophthalmic apparatus 1 further includes a fixation projection system. For example, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor 200 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 200 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor 200 analyzes data processor segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

As described above, in the ophthalmic apparatus 1, the slit 22 (aperture), an imaging site (fundus Ef), and the image sensor 51 (light receiving surface) are arranged at positions substantially conjugate optically each other. The ophthalmic apparatus 1 can acquire a clear image of the imaging site while suppressing the effects due to the unnecessary scattered light, by moving the light receiving opening on the image sensor 51 in conjunction with the irradiated position of the illumination light.

In the ophthalmic apparatus 1 according to the first embodiment, by receiving and capturing the returning light of the illumination light using the image sensor 51 at appropriate timings, the image quality of the image of the subject's eye E acquired based on the light receiving result can be improved without the effects due to the unnecessary scattered light. Here, in the first embodiment, the optical scanner 30 and the image sensor 51 are synchronized with high precision to improve the image quality of the acquired images.

Figure 7:
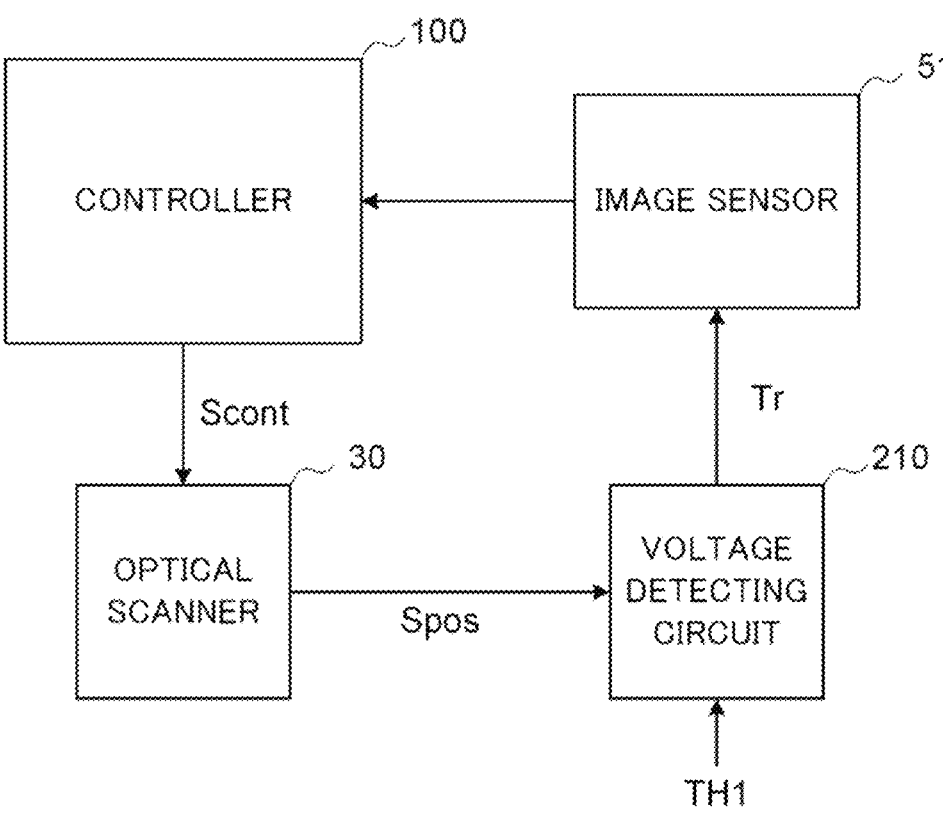
FIG. 7 is an explanatory diagram of an operation of the ophthalmic apparatus according to the first embodiment.

FIG. 7 shows a schematic diagram for explaining the synchronization control of the ophthalmic apparatus 1 according to the first embodiment. In FIG. 7, components similar to those in FIG. 2 are given the same reference numerals. The description of such components is basically omitted.

As described above, the controller 100 controls the deflection angle (angle of the deflection surface relative to a reference angle) of the illumination light changed by the optical scanner 30. The controller 100 controls the deflection angle of the illumination light by outputting a scanner control signal Scont to the optical scanner 30. For example, by outputting the scanner control signal Scont having a desired voltage level to the optical scanner 30, the angle of the deflection surface of the optical scanner 30 can be set to the desired deflection angle.

The optical scanner 30 can output the scanner position signal Spos corresponding to the angle of the deflection surface. For example, the scanner position signal Spos is a signal having a voltage level corresponding to the angle of the deflection surface. By specifying the voltage level of the scanner position signal Spos, the angle of the deflection surface of the optical scanner 30 (deflection angle of the illumination light changed by the optical scanner 30) can be specified.

The voltage detecting circuit 210 detects whether or not the deflection angle of the illumination light changed by the optical scanner 30 is the desired deflection angle based on the voltage level of the scanner position signal Spos from the optical scanner 30, and outputs the trigger signal Tr corresponding to the detection result to the image sensor 51. Specifically, the voltage detecting circuit 210 compares the scanner position signal Spos with a first threshold voltage TH1, and outputs the trigger signal Tr to the image sensor 51. Here, the trigger signal Tr has a voltage level corresponding to the comparison result between the scanner position signal Spos and the first threshold voltage TH1.

The image sensor 51 starts capturing the light receiving result of the returning light of the illumination light on the light receiving surface in synchronization with the change timing (e.g., the rising edge) of the trigger signal Tr from the voltage detecting circuit 210, and transfers the captured light receiving result to the controller 100.

[Operation]

Next, the operation of the ophthalmic apparatus 1 will be described.

Figure 8:
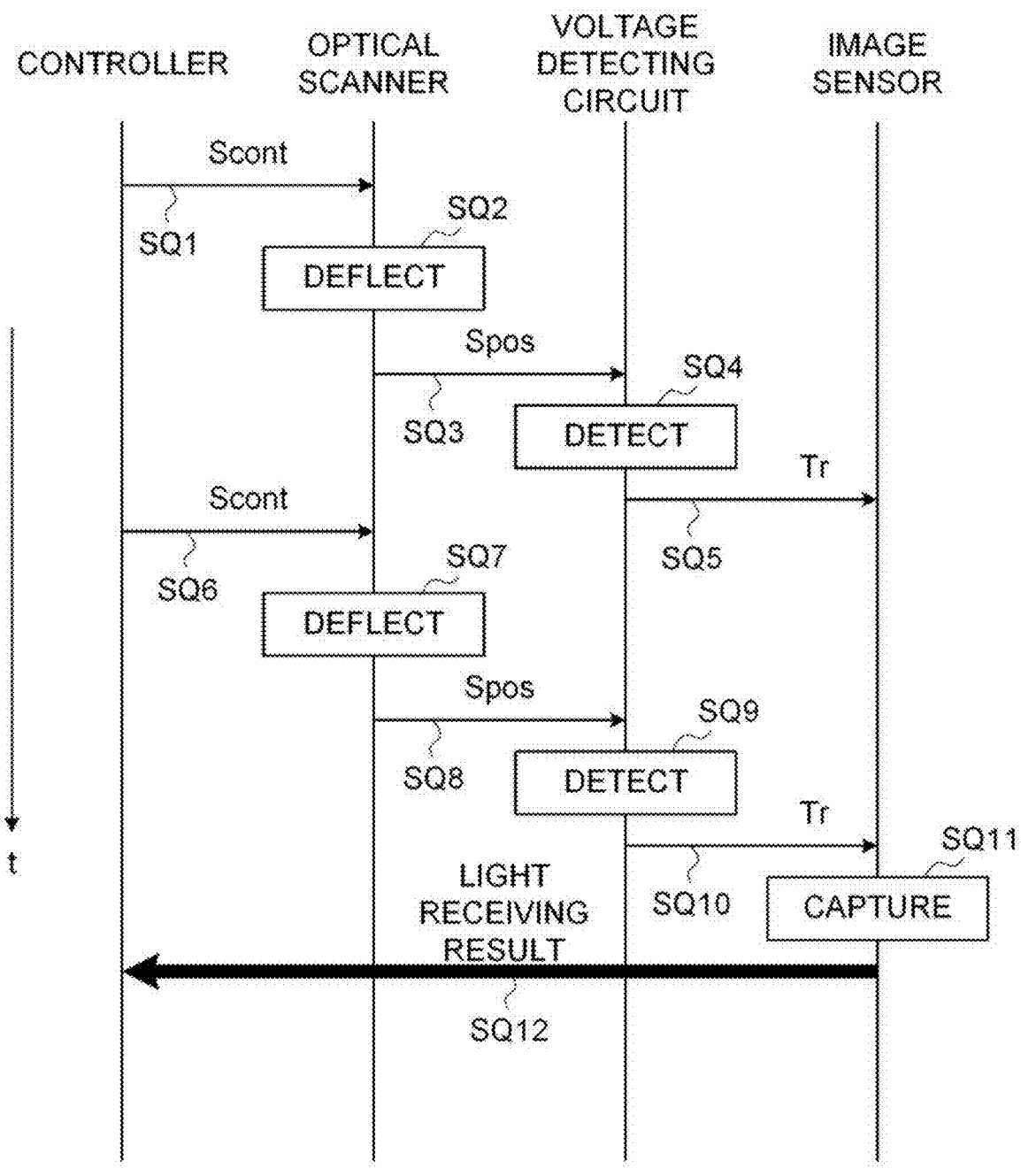
FIG. 8 is a sequence diagram illustrating an example of an operation of the ophthalmic apparatus according to the first embodiment.

FIG. 8 shows an operation example of the ophthalmic apparatus 1 according to the first embodiment. FIG. 8 is a sequence diagram illustrating a sequence of the operation example of the ophthalmic apparatus 1.

First, the controller 100 outputs the scanner control signal Scont to the optical scanner 30 so as to deflect the illumination light at the desired deflection angle (SQ1).

In the optical scanner 30, the orientation of the deflection surface is changed at the deflection angle corresponding to the scanner control signal Scont from the controller 100 (SQ2). Thereby, the predetermined region on fundus Ef can be illuminated with the illumination light. The optical scanner 30 outputs the scanner position signal Spos corresponding to the deflection angle of the deflection surface (SQ3).

The voltage detecting circuit 210 compares the scanner position signal Spos from the optical scanner 30 with the predetermined first threshold voltage TH1. Thereby, the voltage detecting circuit 210 can detect whether or not the light receiving result of the returning light of the illumination light should be captured by the image sensor 51 from the deflection direction of the illumination light changed by the optical scanner 30 (SQ4).

The voltage detecting circuit 210 compares the scanner position signal Spos from the optical scanner 30 with the first threshold voltage TH1, and outputs the trigger signal Tr having a voltage level corresponding to the comparison result (SQ5).

For example, when the scanner position signal Spos is equal to or greater than the first threshold voltage TH1, the trigger signal Tr having a first power supply voltage level ("L" level) is output, and when the scanner position signal Spos is less than the first threshold voltage TH1, the trigger signal Tr having a second power supply voltage level ("H" level) is output. In this case, when the scanner position signal Spos is equal to or greater than the first threshold voltage TH1, the voltage detecting circuit 210 outputs the trigger signal Tr having an "L" level to image sensor 51.

Since the voltage level of the trigger signal Tr from the voltage detecting circuit 210 does not change, the image sensor 51 does not start capturing the light receiving result of the returning light of the illumination light.

Subsequently, the controller 100 outputs the scanner control signal Scont to the optical scanner 30 so as to deflect the illumination light at the next desired deflection angle (SQ6). In some embodiments, the controller 100 outputs the scanner control signals Scont to the optical scanner 30 at predetermined time intervals. In some embodiments, upon receiving notification that the transfer of the light receiving result is completed from the image sensor 51, the controller 100 outputs the scanner control signal Scont for deflecting at the next deflection angle to the optical scanner 30.

Hereinafter, in the same way, in the optical scanner 30, the orientation of the deflection surface is changed at the deflection angle corresponding to the scanner control signal Scont from the controller 100 (SQ7). The optical scanner 30 outputs the scanner position signal Spos corresponding to the deflection angle of the deflection surface (SQ8).

As in SQ4, the voltage detecting circuit 210 compares the scanner position signal Spos from the optical scanner 30 with the first threshold voltage TH1, and detects whether or not the light receiving result of the returning light of the illumination light should be captured by the image sensor 51 (SQ9).

The voltage detecting circuit 210 compares the scanner position signal Spos from the optical scanner 30 with the first threshold voltage TH1, and outputs the trigger signal Tr having a voltage level corresponding to the comparison result (SQ10).

In this case, when the scanner position signal Spos changes from a voltage level equal to or greater than the first threshold voltage TH1 to a voltage level less than the first threshold voltage TH1, the voltage detecting circuit 210 outputs the trigger signal Tr changing from the "L" level to the "H" level to the image sensor 51.

The image sensor 51 starts capturing the light receiving result of the returning light of the illumination light in a predetermined line (see FIG. 6), in synchronization with the rising edge of the trigger signal Tr from the voltage detecting circuit 210 that changes from the "L" level to the "H" level (SQ11).

The image sensor 51 transfers the captured light receiving result to the controller 100 at a predetermined timing (SQ12). The predetermined timing may be a timing determined in advance, or may be a timing determined by the end timing of capturing the predetermined light receiving result. In some embodiments, the controller 100 performs readout control to the image sensor 51 so that the image sensor 51 transfers the light receiving result to the controller 100.

In order to divide the predetermined illumination region of the illumination light on the fundus Ef to sequentially illuminate the divided illumination regions, a series of controls as described above are repeated for each illumination region.

Figure 9:
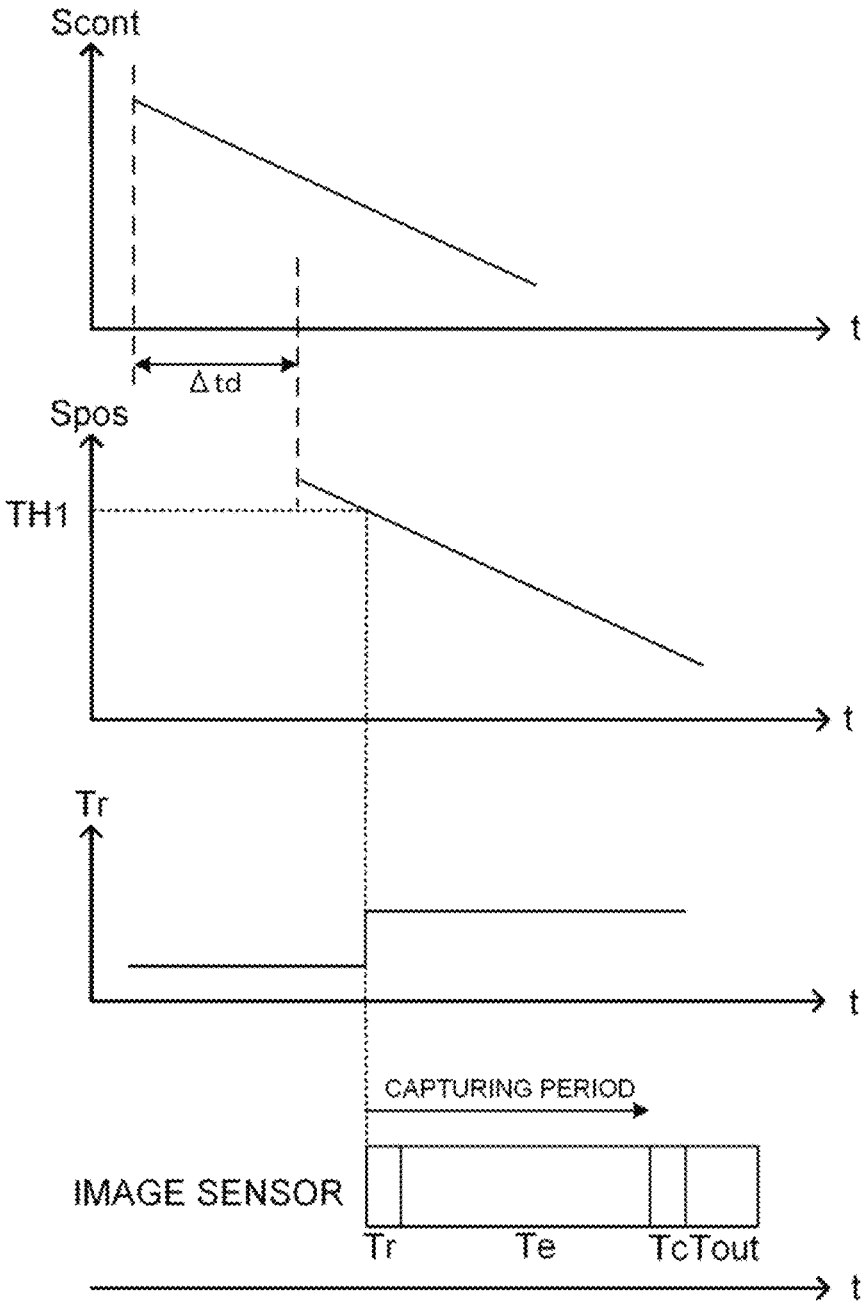
FIG. 9 is an explanatory diagram of an operation of the ophthalmic apparatus according to the first embodiment.

FIG. 9 shows an example of the timing of the synchronization control of the ophthalmic apparatus 1 according to the first embodiment. FIG. 9 schematically represents the relationship among the scanner control signal Scont, the scanner position signal Spos, the trigger signal Tr, and the start timing of capturing the light receiving result performed by the image sensor 51.

In FIG. 9, an example of the timing of the scanner control signal Scont is illustrated in a first timing diagram. In the first timing diagram, the vertical axis represents the voltage level of the scanner control signal Scont, and the horizontal axis represents time "t". Further, an example of the timing of the scanner position signal Spos is illustrated in a second timing diagram. In the second timing diagram, the vertical axis represents the voltage level of the scanner position signal Spos and the horizontal axis represents time "t". Furthermore, an example of the timing of the trigger signal Tr is illustrated in a third timing diagram. In the third timing diagram, the vertical axis represents the voltage level of the trigger signal Tr and the horizontal axis represents time "t".

The controller 100 sequentially changes the illumination region by sequentially outputting the scanner control signal Scont so as to sequentially illuminate a predetermined imaging region on the fundus Ef as shown in FIG. 6. For example, the controller 100 sequentially outputs the scanner control signal Scont to the optical scanner 30 as shown in FIG. 9.

The optical scanner 30 changes the deflection surface so as to have the deflection angle corresponding to the scanner control signal Scont from the controller 100. In this case, the optical scanner 30 changes the deflection surface after a predetermined delay time Δdt has elapsed with reference to the scanner control signal Scont. The optical scanner 30 outputs the scanner position signal Spos corresponding to the deflection angle of the deflection surface.

The voltage detecting circuit 210 compares the voltage level of the scanner position signal Spos with the first threshold voltage TH1, and outputs the trigger signal Tr having a voltage level corresponding to the comparison result to the image sensor 51, as described above. When the voltage level of the scanner position signal Spos changes from a voltage level equal to or greater than the first threshold voltage TH1 to a voltage level less than the first threshold voltage TH1, the voltage detecting circuit 210 changes the voltage level of the trigger signal Tr and outputs the trigger signal Tr having the "H" level.

The image sensor 51 starts capturing the light receiving result of the returning light of the illumination light, in synchronization with the rising edge of the trigger signal Tr from the voltage detecting circuit 210. For example, in the capturing period, as shown in FIG. 6, the reset control is performed in period Tr, the exposure control is performed in period Te, the charge transfer control is performed in period Tc, and the output control is performed in period Tout.

As described above, the timing of capturing the light receiving result of the returning light of the illumination light can be controlled in the image sensor 51, in synchronization with the scanner position signal Spos of the optical scanner 30 that can be controlled by the scanner control signal Scont from the controller 100. This allows to receive and capture the returning light of the illumination light in synchronization with the illumination region of the illumination light with high precision. Therefore, the image quality of the image of the acquired subject's eye E can be improved without the effects of the unnecessary scattered light.

The voltage detecting circuit 210 is an example of the "first voltage detecting circuit" according to the embodiments.

Second Embodiment

The configuration of the ophthalmic apparatus according to the embodiments is not limited to the configuration of the ophthalmic apparatus according to the first embodiment. In the ophthalmic apparatus according to the second embodiment, the image quality of the acquired image of the subject's eye E is improved by synchronizing the optical scanner 30, the image sensor 51, and the light source 10 with high precision.

In the following, the ophthalmic apparatus according to the second embodiment will be described focusing on differences from the ophthalmic apparatus 1 according to the first embodiment.

[Configuration of Optical System]

The configuration of the optical system of the ophthalmic apparatus according to the second embodiment is the same configuration as that of the ophthalmic apparatus 1 according to the first embodiment.

[Configuration of Control System]

Figure 10:
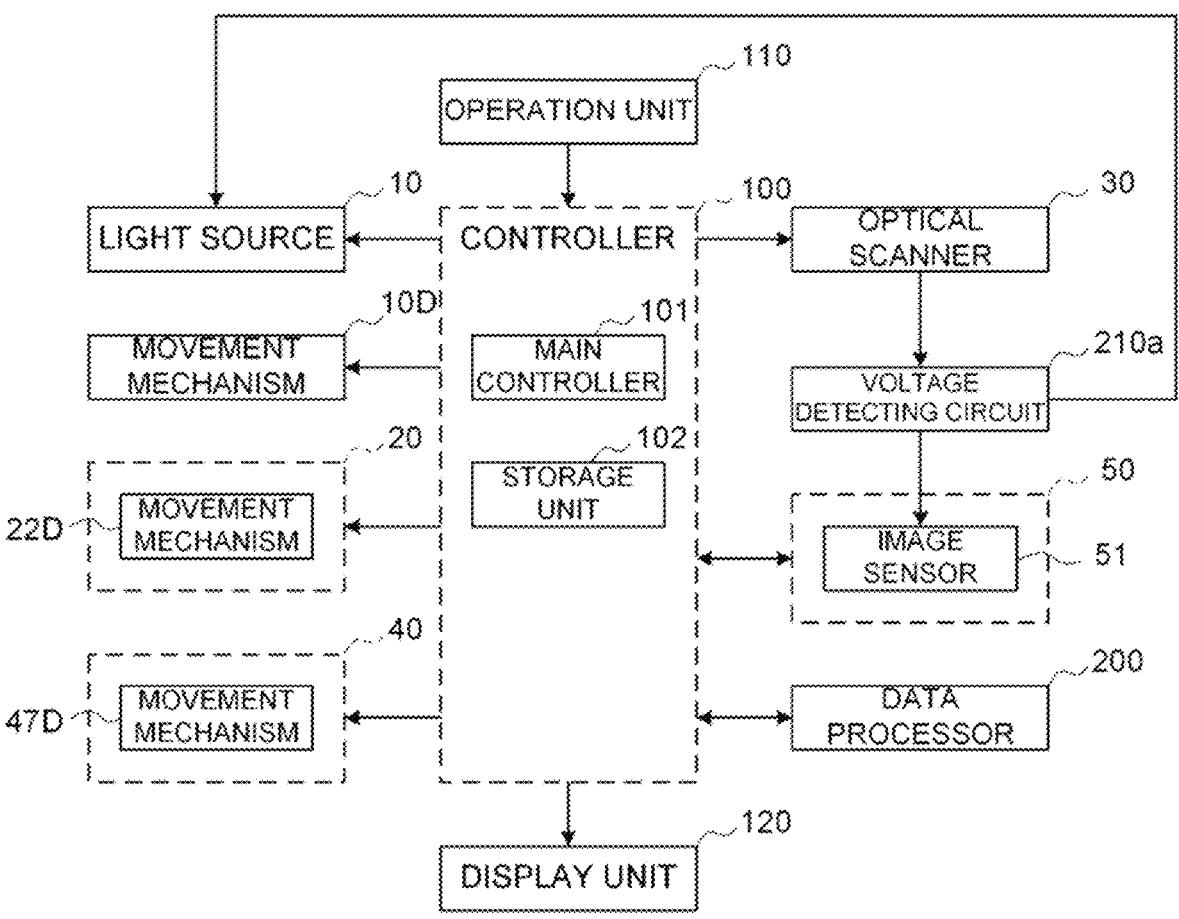
FIG. 10 is a schematic diagram illustrating an example of a configuration of a control system of the ophthalmic apparatus according to a second embodiment.

FIG. 10 shows a block diagram of an example of the configuration of the control system of the ophthalmic apparatus according to second embodiment. In FIG. 10, like reference numerals designate like parts as in FIG. 2, and the same description may not be repeated.

The configuration of the control system of the ophthalmic apparatus according to the second embodiment differs from that of the control system of the ophthalmic apparatus 1 according to the first embodiment in that a voltage detecting circuit 210a is provided in place of the voltage detecting circuit 210.

In addition to the function of the voltage detecting circuit 210, the voltage detecting circuit 210a has a voltage detection function for controlling the light source 10 and an output function of a light source control signal to the light source 10. The voltage detecting circuit 210a synchronizes with the changes in the scanner position signal Spos and outputs the light source control signal LScont for on control and off control of the light source 10.

Figure 11:
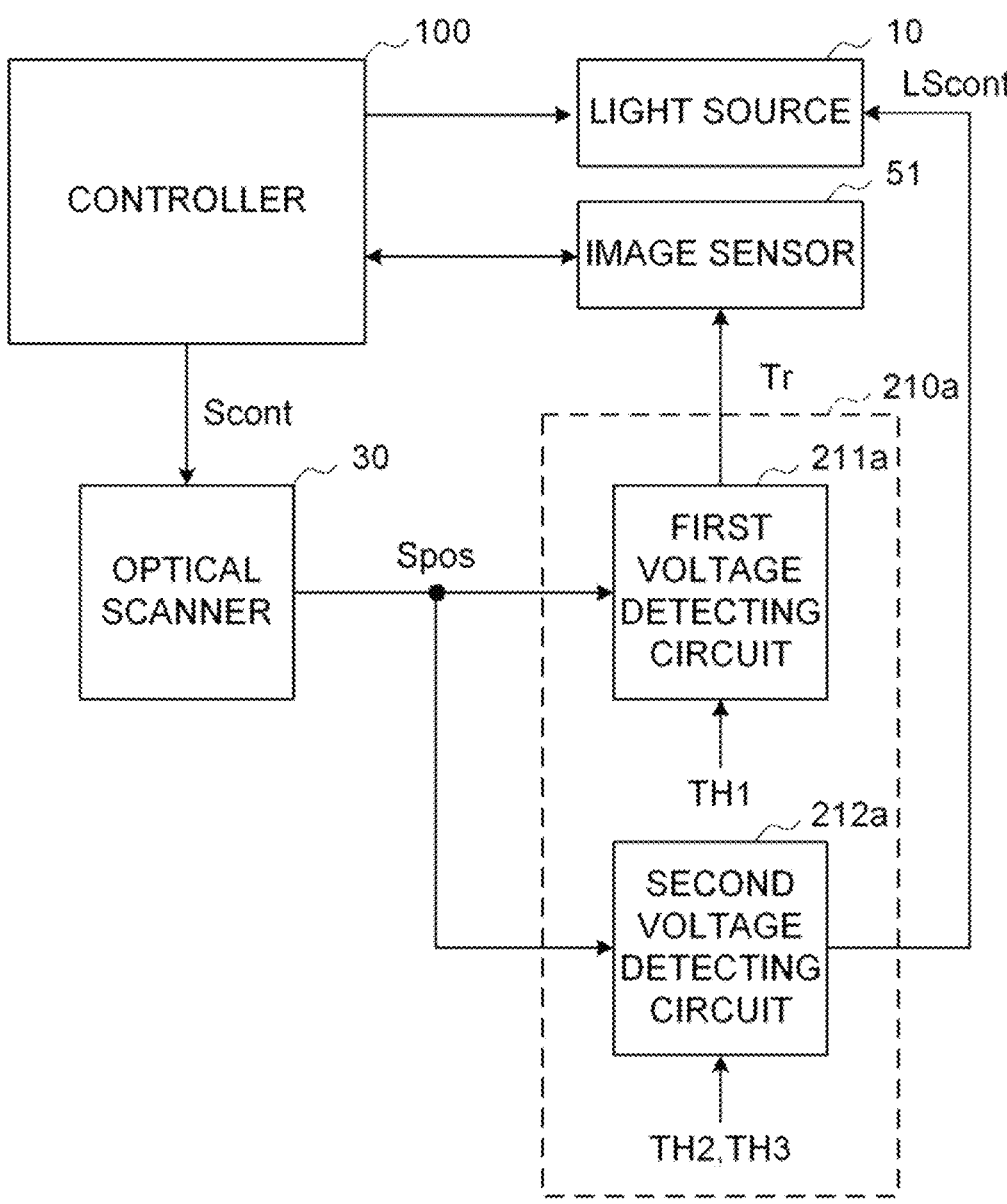
FIG. 11 is an explanatory diagram of an operation of the ophthalmic apparatus according to the second embodiment.

FIG. 11 shows a schematic diagram for explaining the synchronization control of the ophthalmic apparatus according to the second embodiment. In FIG. 11, like reference numerals designate like parts as in FIG. 7 or FIG. 10. The same description may not be repeated.

The voltage detecting circuit 210a includes a first voltage detecting circuit 211a and a second voltage detecting circuit 212a. The first voltage detecting circuit 211a has the same function as the voltage detecting circuit 210 in the first embodiment. That is, the first voltage detecting circuit 211a detects whether or not the deflection angle of the illumination light changed by the optical scanner 30 is the desired deflection angle based on the voltage level of the scanner position signal Spos from the optical scanner 30, and outputs the trigger signal Tr corresponding to the detection result to the image sensor 51. Specifically, the first voltage detecting circuit 211a compares the scanner position signal Spos with the first threshold voltage TH1, and outputs the trigger signal Tr to the image sensor 51. Here, the trigger signal Tr has a voltage level corresponding to the comparison result between the scanner position signal Spos and the first threshold voltage TH1.

The second voltage detecting circuit 212a detects whether or not the deflection angle of the illumination light changed by the optical scanner 30 is the desired deflection angle based on the voltage level of the scanner position signal Spos, and outputs the light source control signal LScont corresponding to the detection result to the light source 10. Specifically, the second voltage detecting circuit 212a compares the scanner position signal Spos with a second threshold voltage TH2, and outputs the light source control signal LScont to the light source 10. Here, the light source control signal LScont has a voltage level corresponding to the comparison result between the scanner position signal Spos and the second threshold voltage TH2. For example, when the scanner position signal Spos is equal to or greater than the second threshold voltage TH2, the second voltage detecting circuit 212a outputs the light source control signal LScont having the "L" level. The second threshold voltage TH2 is, for example, the threshold voltage for switching the light source 10 from the off-state to the on-state.

Further, the second voltage detecting circuit 212a compares the scanner position signal Spos with a third threshold voltage TH3, and outputs the light source control signal LScont to the light source 10. Here, the light source control signal LScont has a voltage level corresponding to the comparison result between the scanner position signal Spos and the third threshold voltage TH3. For example, when the scanner position signal Spos is less than the third threshold voltage TH3, the second voltage detecting circuit 212a outputs the light source control signal LScont having the "L" level. The third threshold voltage TH3 is, for example, the threshold voltage for switching the light source 10 from the on-state to the off-state.

It should be noted that when the scanner position signal Spos is less than the second threshold voltage TH2 and is equal to or greater than the third threshold voltage TH3, the second voltage detecting circuit 212a outputs the light source control signal LScont having the "H" level.

The function of such the second voltage detecting circuit 212a can be realized, for example, with one or more known comparator circuits and an RS flip-flop circuit. In order to capture the light receiving result using the image sensor 51 during the period when the light source 10 is in the on-state, the first threshold voltage TH1 may be a voltage between the second threshold voltage TH2 and the third threshold voltage TH3. In some embodiments, the voltage level of the first threshold voltage TH1 is approximately equal to the voltage level of the second threshold voltage TH2.

As in the first embodiment, the image sensor 51 starts capturing the light receiving result of the returning light of the illumination light on the light receiving surface in synchronization with the change timing (e.g., the rising edge) of the trigger signal Tr from the first voltage detecting circuit 211a, and transfers the captured light receiving result to the controller 100.

The light source 10 is switched from the off-state (non-lighting state) to the on-state (lighting state), in synchronization with a first change timing (e.g., rising edge) of the light source control signal LScont from the second voltage detecting circuit 212a. Further, the light source 10 is switched from the on-state to the off-state, in synchronization with a second change timing (e.g., falling edge) of the light source control signal LScont from the second voltage detecting circuit 212a.

[Operation]

Next, the operation of the ophthalmic apparatus according to the second embodiment will be described.

Figure 12:
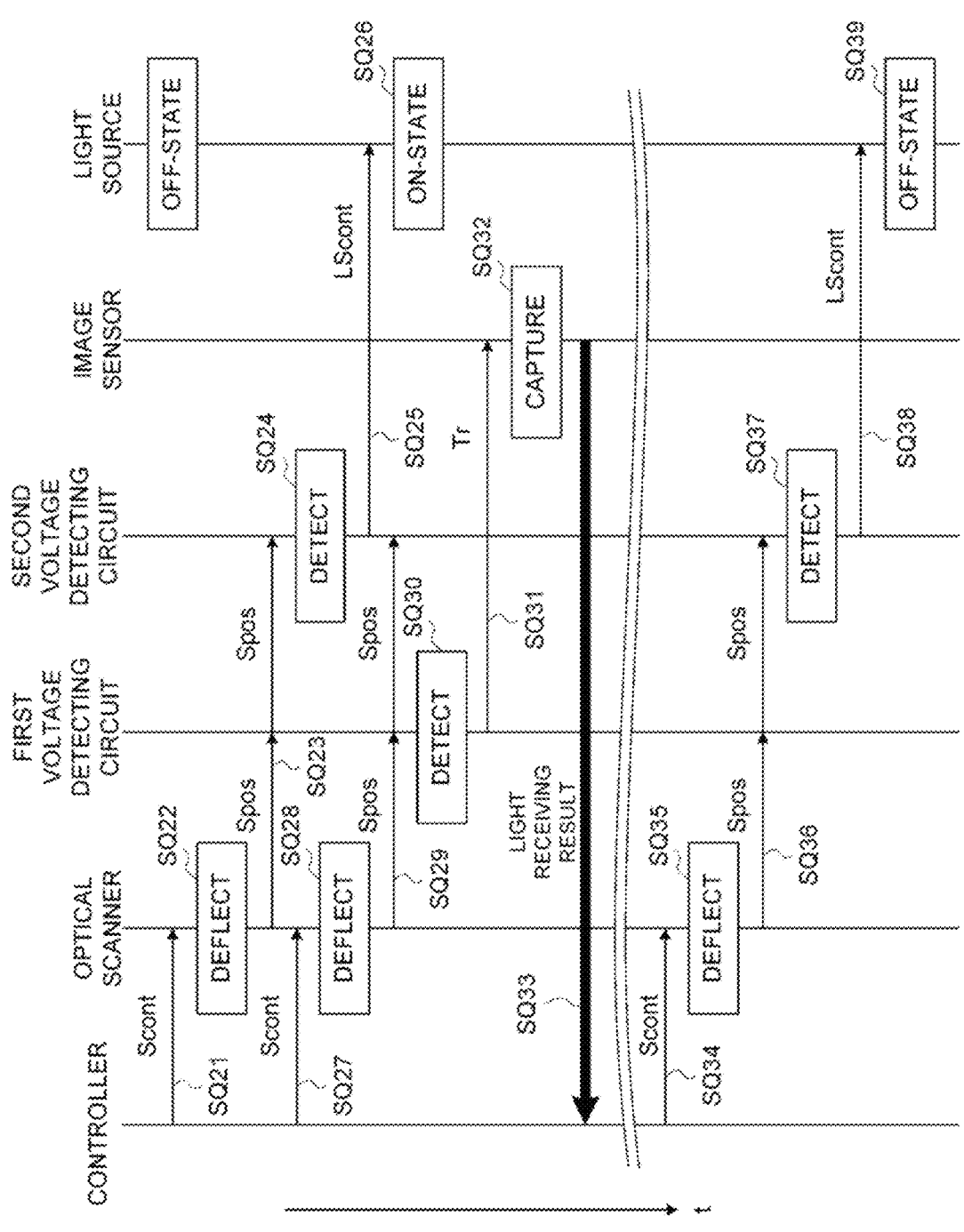
FIG. 12 is a sequence diagram illustrating an example of an operation of the ophthalmic apparatus according to the second embodiment.

FIG. 12 shows an operation example of the ophthalmic apparatus according to the second embodiment. FIG. 12 is a sequence diagram illustrating a sequence of the operation example of the ophthalmic apparatus according to the second embodiment. It is assumed that the following control is performed when the light source 10 is in the off-state.

First, as in SQ1, the controller 100 outputs the scanner control signal Scont to the optical scanner 30 so as to deflect the illumination light at the desired deflection angle (SQ21).

In the optical scanner 30, as in SQ2, the orientation of the deflection surface is changed at the deflection angle corresponding to the scanner control signal Scont from the controller 100 (SQ22). The optical scanner 30 outputs the scanner position signal Spos corresponding to the deflection angle of the deflection surface, as in SQ3 (SQ23).

It is when the voltage level of the scanner position signal Spos changes from a voltage level equal to or greater than the second threshold voltage TH2 to a voltage level less than the second threshold voltage TH2 (however, the voltage level equal to or greater than the first threshold voltage TH1). Thus, the first voltage detecting circuit 211*a* does not change the voltage level of the trigger signal Tr, and the second voltage detecting circuit 212*a* changes the voltage level of the light source control signal LScont (SQ24). The second voltage detecting circuit 212*a* outputs the light source control signal LScont that has been changed to the "H" level to the light source 10 (SQ25).

The light source 10 is switched from the off-state to the on-state, in synchronization with the change timing (rising edge) of the light source control signal LScont from the second voltage detecting circuit 212*a* (SQ26).

For example, the controller 100 outputs the scanner control signal Scont to the optical scanner 30 so as to deflect the illumination light at the next desired deflection angle, after a predetermined time interval from SQ21 (SQ27). In the optical scanner 30, the orientation of the deflection surface is changed at the deflection angle corresponding to the scanner control signal Scont from the controller 100 (SQ28). The optical scanner 30 outputs the scanner position signal Spos corresponding to the deflection angle of the deflection surface (SQ29).

When the voltage level of the scanner position signal Spos changes from a voltage level equal to or greater than the first threshold voltage TH1 to a voltage level less than the first threshold voltage TH1 (however, the voltage level greater than the third threshold voltage TH3), the first voltage detecting circuit 211*a* changes the voltage level of the trigger signal Tr and the second voltage detecting circuit 212*a* does not change the voltage level of the light source control signal LScont (SQ30). The first voltage detecting circuit 211*a* outputs the trigger signal Tr that has been changed to the "H" level to the image sensor 51 (SQ31).

The image sensor 51 starts capturing the light receiving result of the returning light of the in a predetermined line, in synchronization with the rising edge of the trigger signal Tr from the voltage detecting circuit 210.

The image sensor 51 transfers the captured light receiving result to the controller 100 at a predetermined timing (SQ33).

Hereinafter, in the same way, in order to divide the predetermined illumination region of the illumination light on the fundus Ef to sequentially illuminate the divided illumination regions, a series of controls as described above are repeated for each illumination region.

After that, for example, the controller 100 outputs the scanner control signal Scont to the optical scanner 30 so as to deflect the illumination light at the next desired deflection angle (SQ34). In the optical scanner 30, the orientation of the deflection surface is changed at the deflection angle corresponding to the scanner control signal Scont from the controller 100 (SQ35). The optical scanner 30 outputs the scanner position signal Spos corresponding to the deflection angle of the deflection surface (SQ36).

When the voltage level of the scanner position signal Spos changes from a voltage level equal to or greater than the third threshold voltage TH3 to a voltage level less than the third threshold voltage TH3, the first voltage detecting circuit 211*a* does not change the voltage level of the trigger signal Tr and the second voltage detecting circuit 212*a* changes the voltage level of the light source control signal LScont (SQ37). The second voltage detecting circuit 212*a* outputs the light source control signal LScont that has been changed to the "L" level to the light source 10 (SQ38).

The light source 10 is switched from the on-state to the off-state, in synchronization with the change timing (falling edge) of the light source control signal LScont from the second voltage detecting circuit 212*a* (SQ39).

Figure 13:
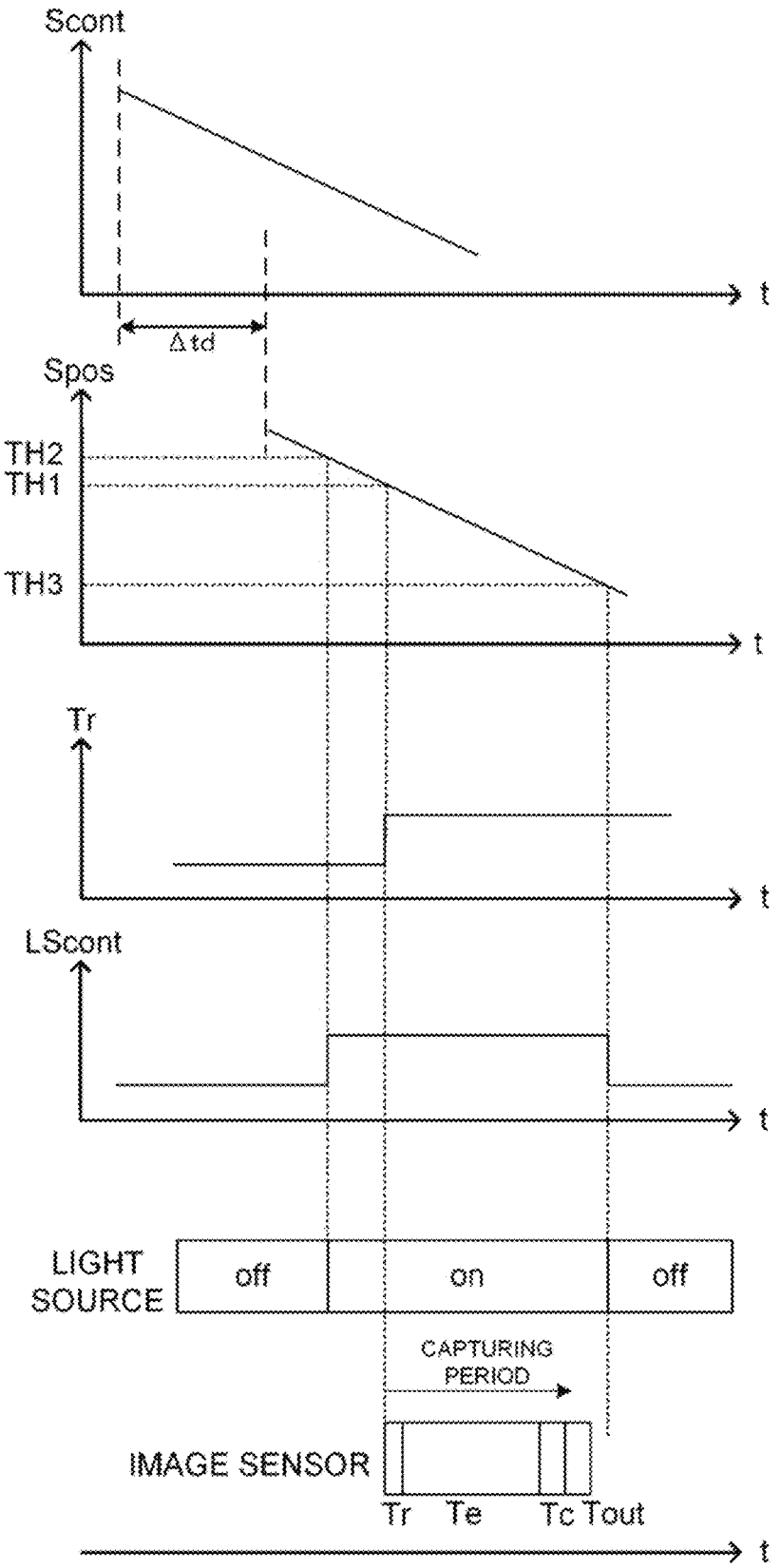
FIG. 13 is an explanatory diagram of an operation of the ophthalmic apparatus according to the second embodiment.

FIG. 13 shows an example of the timing of the synchronization control of the ophthalmic apparatus according to the second embodiment. FIG. 13 schematically represents the relationship among the scanner control signal Scont, the scanner position signal Spos, the trigger signal Tr, the light source control signal LScont, and the start timing of capturing the light receiving result performed by the image sensor 51.

In FIG. 13, an example of the timing of the scanner control signal Scont is illustrated in the first timing diagram. Further, an example of the timing of the scanner position signal Spos is illustrated in the second timing diagram. Furthermore, an example of the timing of the trigger signal Tr is illustrated in the third timing diagram. Furthermore, an example of the timing of the light source control signal LScont is illustrated in the third timing diagram. In the third timing diagram, the vertical axis represents the voltage level of the light source control signal LScont, and the horizontal axis represents time "t".

The controller 100 sequentially changes the illumination region by sequentially outputting the scanner control signal Scont so as to sequentially illuminate a predetermined imaging region on the fundus Ef as shown in FIG. 6. For example, the controller 100 sequentially outputs the scanner control signal Scont to the optical scanner 30 as shown in FIG. 13.

The optical scanner 30 changes the deflection surface so as to have the deflection angle corresponding to the scanner control signal Scont from the controller 100. In this case, the optical scanner 30 changes the deflection surface after a predetermined delay time Δdt has elapsed with reference to the scanner control signal Scont. The optical scanner 30 outputs the scanner position signal Spos corresponding to the deflection angle of the deflection surface.

First, the second voltage detecting circuit 212*a* compares the voltage level of the scanner position signal Spos with the second threshold voltage TH2, and outputs the light source control signal LScont having a voltage level corresponding to the comparison result to the light source 10, as described above. When the voltage level of the scanner position signal Spos changes from a voltage level equal to or greater than the second threshold voltage TH2 to a voltage level less than the second threshold voltage TH2, the second voltage detecting circuit 212*a* changes the voltage level of the light source control signal LScont and outputs the light source control signal LScont having the "H" level.

The light source 10 is switched from the off-state to the on-state, in synchronization with the rising edge of the light source control signal LScont from the second voltage detecting circuit 212*a*.

Subsequently, the first voltage detecting circuit 211*a* compares the voltage level of the scanner position signal Spos with the first threshold voltage TH1, and outputs the trigger signal Tr having a voltage level corresponding to the comparison result to the image sensor 51, as described above. When the voltage level of the scanner position signal Spos changes from a voltage level equal to or greater than the first threshold voltage TH1 (however, TH1>TH3) to a voltage level less than the first threshold voltage TH1, the first voltage detecting circuit 211*a* changes the voltage level of the trigger signal Tr and outputs the trigger signal Tr having the "H" level.

The image sensor 51 starts capturing the light receiving result of the returning light of the illumination light, in synchronization with the rising edge of the trigger signal Tr from the first voltage detecting circuit 211*a*. For example, in the capturing period, as shown in FIG. 6, the reset control is performed in period Tr, the exposure control is performed in period Te, the charge transfer control is performed in period Tc, and the output control is performed in period Tout.

For example, after the transfer of the light receiving result to the controller 100 using the image sensor 51 is completed, the controller 100 outputs the scanner control signal Scont to the optical scanner 30 to change the orientation of the deflection surface. In this case, the second voltage detecting circuit 212a compares the voltage level of the scanner position signal Spos with the third threshold voltage TH3, and outputs the light source control signal LScont having a voltage level corresponding to the comparison result to the light source 10, as described above. When the voltage level of the scanner position signal Spos changes from a voltage level equal to or greater than the third threshold voltage TH3 to a voltage level less than the third threshold voltage TH3, the second voltage detecting circuit 212a changes the voltage level of the light source control signal LScont and outputs the light source control signal LScont having the "L" level.

The light source 10 is switched from the on-state to the off-state, in synchronization with the falling edge of the light source control signal LScont from the second voltage detecting circuit 212a.

It should be noted that the case where the light source 10 is switched to the off-state based on the voltage level of the scanner position signal Spos in the second embodiments. However, the configuration according to the embodiments is not limited thereto. For example, after a predetermined period has elapsed after the light source 10 is switched to the on-state based on the voltage level of the scanner position signal Spos, the controller 100 may control the light source 10 to switch to the off-state.

As described above, the capturing timing of the light receiving result of the returning light of the illumination light using the image sensor 51, and the irradiation timing of the illumination light using the light source 10 can be controlled, in synchronization with the scanner position signal Spos of the optical scanner 30 that can be controlled by the scanner control signal Scont from the controller 100. This allows to receive and capture the returning light of the illumination light in synchronization with the illumination region of the illumination light with high precision. Therefore, the image quality of the image of the acquired subject's eye E can be improved without the effects of the unnecessary scattered light.

In addition, the image sensor 51 can start capturing the light receiving result and end capturing the light receiving result, during the period when the light source 10 is in the on-state. Thereby, the effect of unnecessary scattered light can be reliably eliminated and the image quality of the subject's eye E can be further improved.

The first voltage detecting circuit 211a is an example of the "first voltage detecting circuit" according to the embodiments. The second voltage detecting circuit 212a is an example of the "second voltage detecting circuit" according to the embodiments. The second threshold voltage TH2 or the third threshold voltage TH3 is an example of the "second threshold voltage" according to the embodiments.

[Actions and Effects]

The Actions and the effects of an ophthalmic apparatus, a method of controlling the same, and a program according to the embodiments will be described.

An ophthalmic apparatus (1) according to some embodiments includes a light source (10), an illumination optical system (20), an optical scanner (30), an imaging optical system (40), and a controller (100, main controller 101). The illumination optical system is configured to generate slit-shaped illumination light using light from the light source. The optical scanner is configured to deflect the illumination light to guide the illumination light to a fundus (Ef) of a subject's eye (E). The imaging optical system is configured to guide returning light of the illumination light from the fundus to an image sensor (51), the image sensor capturing light receiving result of a region on a light receiving surface corresponding to an illumination region of the illumination light on the fundus, using a rolling shutter method. The controller is configured to control a deflection angle of the illumination light of the optical scanner. The optical scanner is configured to output a scanner position signal (Spos) corresponding to the deflection angle of the illumination light. The image sensor is configured to start capturing the light receiving result of the returning light in synchronization with the scanner position signal.

According to such a configuration, the optical scanner and the image sensor can be synchronized with high precision using a simple configuration. This allows the unnecessary scattered light to be prevented from being captured and allows to acquire the high-quality image of the subject's eye formed based on the light receiving result of the image sensor.

Some embodiments include a first voltage detecting circuit (voltage detecting circuit 210, first voltage detecting circuit 211a) changing a trigger signal (Tr) in accordance with a comparison result between the scanner position signal and a first threshold voltage (TH1). The image sensor is configured to start capturing the light receiving result in synchronization with the change in the trigger signal.

According to such a configuration, the trigger signal is changed based on the voltage level of the scanner position signal, and the image sensor starts capturing the light receiving result in synchronization with the change in the trigger signal. This allows to synchronize the optical scanner and the image sensor with high precision using a simple configuration.

In some embodiments, the controller is configured to output a scanner control signal (Scont) to the optical scanner to deflect the illumination light at a deflection angle corresponding to the scanner control signal.

According to such a configuration, the scanner position signal corresponding to the deflection angle can be generated using the scanner control signal. This allows the image sensor to start capturing the light receiving result in synchronization with the scanner control signal by the controller.

In some embodiments, the light source is configured to be switched from an on-state to an off-state or from the off-state to the on-state in synchronization with the scanner position signal.

According to such a configuration, the optical scanner, the image sensor, and the light source can be synchronized with high precision using a simple configuration. This allows the unnecessary scattered light to be prevented from being captured and allows to acquire the high-quality image of the subject's eye formed based on the light receiving result of the image sensor.

Some embodiments include a second voltage detecting circuit (212a) configured to change a light source control signal (LScont) for on/off control of the light source in accordance with a comparison result between the scanner position signal and a second threshold voltage (TH2, the third threshold voltage TH3). The light source is configured to be switched from the on-state to the off-state or from the off-state to the on-state in synchronization with the change in the light source control signal.

According to such a configuration, the light source control signal is changed based on the voltage level of the scanner position signal, and the on/off control for the light source is performed in synchronization with the change in the trigger signal. This allows to synchronize the optical scanner, the image sensor, and the light source with high precision using a simple configuration.

In some embodiments, the image sensor is configured to start capturing the light receiving result and to end capturing the light receiving result during the period when the light source is in the on-state.

According to such a configuration, the effect of unnecessary scattered light can be eliminated reliably, and the image quality of the image of the subject's eye can be further improved.

In some embodiments, the image sensor is a CMOS image sensor.

According to such a configuration, the optical scanner and the image sensor can be synchronized with high precision at low cost, using a simple configuration.

A method of controlling an ophthalmic apparatus (1) according to some embodiments, the ophthalmic apparatus including: a light source (10); an illumination optical system (20) configured to generate slit-shaped illumination light using light from the light source; an optical scanner (30) configured to deflect the illumination light to guide the illumination light to a fundus of a subject's eye; an imaging optical system (40) configured to guide returning light of the illumination light from the fundus to an image sensor (51), the image sensor capturing light receiving result of a region on a light receiving surface corresponding to an illumination region of the illumination light on the fundus, the illumination region being moved by the optical scanner; and a controller (100, main controller 101) configured to control a deflection angle of the illumination light of the optical scanner, is a method of controlling an ophthalmic apparatus. The method of controlling the ophthalmic apparatus includes a first output step of outputting a scanner position signal (Spos) corresponding to a deflection angle of the illumination light by the optical scanner, and a light receiving result acquisition step of starting capturing light receiving result of the returning light in synchronization with the scanner position signal by the image sensor.

According to such a method, the optical scanner and the image sensor can be synchronized with high precision while simplifying the configuration of the ophthalmic apparatus. This allows the unnecessary scattered light to be prevented from being captured and allows to acquire the high-quality image of the subject's eye formed based on the light receiving result of the image sensor.

Some embodiments further include a first voltage detecting step of changing a trigger signal in accordance with a comparison result between the scanner position signal and a first threshold voltage (TH1). The light receiving result acquisition step is performed to start capturing the light receiving result in synchronization with the change in the trigger signal by the image sensor.

According to such a method, the trigger signal is changed based on the voltage level of the scanner position signal, and the image sensor starts capturing the light receiving result in synchronization with the change in the trigger signal. This allows to synchronize the optical scanner and the image sensor with high precision while simplifying the configuration of the ophthalmic apparatus.

Some embodiments include further include a second output step of outputting a scanner control signal (Scont) to the optical scanner by the controller. The optical scanner is configured to deflect the illumination light at a deflection angle corresponding to the scanner control signal.

According to such a method, the scanner position signal corresponding to the deflection angle can be generated using the scanner control signal. This allows the image sensor to start capturing the light receiving result in synchronization with the scanner control signal by the controller.

Some embodiments further include a light source control step of switching the light source from an on-state to an off-state or from the off-state to the on-state in synchronization with the scanner position signal.

According to such a method, the, the optical scanner, the image sensor, and the light source can be synchronized with high precision while simplifying the configuration of the ophthalmic apparatus. This allows the unnecessary scattered light to be prevented from being captured and allows to acquire the high-quality image of the subject's eye formed based on the light receiving result of the image sensor.

Some embodiments further include a second voltage detecting step of changing a light source control signal (LScont) for on/off control of the light source in accordance with a comparison result between the scanner position signal and a second threshold voltage (TH2, the third threshold voltage TH3). The light source control step is performed to switching the light source from the on-state to the off-state or from the off-state to the on-state in synchronization with the change in the light source control signal.

According to such a method, the light source control signal is changed based on the voltage level of the scanner position signal, and the on/off control for the light source is performed in synchronization with the change in the trigger signal. This allows to synchronize the optical scanner, the image sensor, and the light source with high precision while simplifying the configuration of the ophthalmic apparatus.

In some embodiments, the light receiving acquisition step is performed to start capturing the light receiving result and to end capturing the light receiving result by the image sensor during the period when the light source is in the on-state.

According to such a method, the effect of unnecessary scattered light can be eliminated reliably, and the image quality of the image of the subject's eye can be further improved.

In some embodiments, the image sensor is a CMOS image sensor.

According to such a method, the optical scanner and the image sensor can be synchronized with high precision at low cost, while simplifying the configuration of the ophthalmic apparatus.

In some embodiments, a program is a program of causing a computer to execute each step of the method of controlling the ophthalmic apparatus of any one of the above.

According to such a program, the optical scanner and the image sensor can be synchronized with high precision using a simple configuration. This allows the unnecessary scattered light to be prevented from being captured and allows to acquire the high-quality image of the subject's eye formed based on the light receiving result of the image sensor.

The above-described some embodiments or the modification examples thereof are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include an axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The intraocular pressure measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus described above is provided. Such a program can be stored in any non-transitory computer-readable recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
a light source;
an illumination optical system including a slit that can be arranged at a position substantially conjugate optically to a fundus of a subject's eye and is configured to be movable in an optical axis direction in accordance with a state of the subject's eye, and configured to generate slit-shaped illumination light by irradiating light from the light source onto the slit;
an optical scanner configured to deflect the illumination light to guide the illumination light to a fundus of the subject's eye;
an imaging optical system configured to guide returning light of the illumination light from the fundus to an image sensor, the image sensor capturing a light receiving result on a light receiving surface corresponding to an illumination region of the illumination light on the fundus, the illumination region being moved by the optical scanner; and
a controller configured to control a deflection angle of the illumination light of the optical scanner, wherein
at least one of a relative position of the light source to the slit, or a relative orientation of the light source to the slit is configured to be changeable,
the optical scanner is configured to output a scanner position signal corresponding to the deflection angle of the illumination light, and
the image sensor is configured to start capturing the light receiving result of the returning light in synchronization with the scanner position signal.

2. The ophthalmic apparatus of claim 1, further comprising
a first voltage detecting circuit configured to change a trigger signal in accordance with a comparison result between the scanner position signal and a first threshold voltage, wherein
the image sensor is configured to start capturing the light receiving result in synchronization with the change in the trigger signal.

3. The ophthalmic apparatus of claim 1, wherein
the controller is configured to output a scanner control signal to the optical scanner to deflect the illumination light at a deflection angle corresponding to the scanner control signal.

4. The ophthalmic apparatus of claim 1, wherein
the light source is configured to be switched from an on-state to an off-state or from the off-state to the on-state in synchronization with the scanner position signal.

5. The ophthalmic apparatus of claim 4, further comprising:
a second voltage detecting circuit configured to change a light source control signal for on/off control of the light source in accordance with a comparison result between the scanner position signal and a second threshold voltage, wherein
the light source is configured to be switched from the on-state to the off-state or from the off-state to the on-state in synchronization with the change in the light source control signal.

6. The ophthalmic apparatus of claim 5, wherein
the image sensor is configured to start capturing the light receiving result and to end capturing the light receiving result during the period when the light source is in the on-state.

7. The ophthalmic apparatus of claim 1, wherein
the image sensor is a CMOS image sensor.

8. A method of controlling an ophthalmic apparatus comprising:
a light source;
an illumination optical system including a slit that can be arranged at a position substantially conjugate optically to a fundus of a subject's eye and is configured to be movable in an optical axis direction in accordance with a state of the subject's eye, and configured to generate slit-shaped illumination light by irradiating light from the light source onto the slit;
an optical scanner configured to deflect the illumination light to guide the illumination light to a fundus of the subject's eye;
an imaging optical system configured to guide returning light of the illumination light from the fundus to an image sensor, the image sensor capturing a light receiving result on a light receiving surface corresponding to an illumination region of the illumination light on the fundus, the illumination region being moved by the optical scanner; and a controller configured to control a deflection angle of the illumination light of the optical scanner, wherein at least one of a relative position of the light source to the slit, or a relative orientation of the light source to the slit is configured to be changeable, the method comprising:

a first output step of outputting a scanner position signal corresponding to a deflection angle of the illumination light by the optical scanner, and a light receiving result acquisition step of starting capturing light receiving result of the returning light in synchronization with the scanner position signal by the image sensor.

9. The method of controlling the ophthalmic apparatus of claim 8, further comprising a first voltage detecting step of changing a trigger signal in accordance with a comparison result between the scanner position signal and a first threshold voltage, wherein the light receiving result acquisition step is performed to start capturing the light receiving result in synchronization with the change in the trigger signal by the image sensor.

10. The method of controlling the ophthalmic apparatus of claim 8, further comprising a second output step of outputting a scanner control signal to the optical scanner by the controller, wherein the optical scanner is configured to deflect the illumination light at a deflection angle corresponding to the scanner control signal.

11. The method of controlling the ophthalmic apparatus of claim 8, further comprising a light source control step of switching the light source from an on-state to an off-state or from the off-state to the on-state in synchronization with the scanner position signal.

12. The method of controlling the ophthalmic apparatus of claim 11, further comprising a second voltage detecting step of changing a light source control signal for on/off control of the light source in accordance with a comparison result between the scanner position signal and a second threshold voltage, wherein the light source control step is performed to switching the light source from the on-state to the off-state or from the off-state to the on-state in synchronization with the change in the light source control signal.

13. The method of controlling the ophthalmic apparatus of claim 12, wherein the light receiving acquisition step is performed to start capturing the light receiving result and to end capturing the light receiving result by the image sensor during the period when the light source is in the on-state.

14. The method of controlling the ophthalmic apparatus of claim 8, wherein the image sensor is a CMOS image sensor.

15. A non-transitory computer-readable recording medium storing a program of causing a computer to execute each step of a method of controlling an ophthalmic apparatus, wherein the ophthalmic apparatus comprises:

a light source;

an illumination optical system including a slit that can be arranged at a position substantially conjugate optically to a fundus of a subject's eye and is configured to be movable in an optical axis direction in accordance with a state of the subject's eye, and configured to generate slit-shaped illumination light by irradiating light from the light source onto the slit;

an optical scanner configured to deflect the illumination light to guide the illumination light to a fundus of the subject's eye;

an imaging optical system configured to guide returning light of the illumination light from the fundus to an image sensor, the image sensor capturing a light receiving result on a light receiving surface corresponding to an illumination region of the illumination light on the fundus, the illumination region being moved by the optical scanner; and a controller configured to control a deflection angle of the illumination light of the optical scanner, wherein at least one of a relative position of the light source to the slit, or a relative orientation of the light source to the slit is configured to be changeable, and the method of controlling the ophthalmic apparatus comprises:

a first output step of outputting a scanner position signal corresponding to a deflection angle of the illumination light by the optical scanner, and a light receiving result acquisition step of starting capturing light receiving result of the returning light in synchronization with the scanner position signal by the image sensor.

* * * * *